United States Patent
Samura et al.

(10) Patent No.: US 12,385,007 B2
(45) Date of Patent: Aug. 12, 2025

(54) METHOD FOR PRODUCING FIBRIN SHEET

(71) Applicant: OSAKA UNIVERSITY, Suita (JP)

(72) Inventors: Takaaki Samura, Suita (JP); Shigeru Miyagawa, Suita (JP); Yoshiki Sawa, Suita (JP); Junya Yokoyama, Suita (JP)

(73) Assignee: OSAKA UNIVERSITY, Suita (JP)

( * ) Notice: Subject to any disclaimer, the term of this patent is extended or adjusted under 35 U.S.C. 154(b) by 805 days.

(21) Appl. No.: 17/765,637

(22) PCT Filed: Sep. 9, 2020

(86) PCT No.: PCT/JP2020/034096
§ 371 (c)(1),
(2) Date: Mar. 31, 2022

(87) PCT Pub. No.: WO2021/065395
PCT Pub. Date: Apr. 8, 2021

(65) Prior Publication Data
US 2022/0372437 A1     Nov. 24, 2022

(30) Foreign Application Priority Data
Oct. 1, 2019   (JP) ................................ 2019-181395

(51) Int. Cl.
*C12N 5/00* (2006.01)
*C07K 14/75* (2006.01)

(52) U.S. Cl.
CPC ............ *C12N 5/0068* (2013.01); *C07K 14/75* (2013.01); *C12N 2533/54* (2013.01); *C12N 2533/56* (2013.01)

(58) Field of Classification Search
CPC ................................................... C12N 5/0068
See application file for complete search history.

(56) References Cited

U.S. PATENT DOCUMENTS

2016/0058908 A1    3/2016  Oohashi et al.

FOREIGN PATENT DOCUMENTS

JP     2011-172925 A     9/2011

OTHER PUBLICATIONS

Ho, (2006) Tissue Engineering, vol. 12, No. 6, pp. 1587-1595 (Year: 2006).*

(Continued)

*Primary Examiner* — Mark L Shibuya
(74) *Attorney, Agent, or Firm* — Sughrue Mion, PLLC

(57) ABSTRACT

A method for producing a fibrin sheet containing at least one selected from the group consisting of cells and drugs in a fibrin gel, the method comprising:
a step 1 of applying a fibrinogen solution containing at least one selected from the group consisting of cells and drugs and fibrinogen dropwise onto a surface of a substrate made of a gelatin hydrogel;
a step 2 of adding thrombin to the fibrinogen solution on the surface of the substrate;
a step 3 of placing a support film on and in contact with a top surface of the fibrinogen solution to which the thrombin has been added;
a step 4 of forming a fibrin sheet containing the at least one selected from the group consisting of cells and drugs in a fibrin gel between the substrate and the support film by a reaction between the fibrinogen and the thrombin; and
a step 5 of melting the substrate at a temperature not lower than a melting temperature of the gelatin hydrogel to separate, from the substrate, the fibrin sheet supported by the support film.

5 Claims, 3 Drawing Sheets

(56) References Cited

OTHER PUBLICATIONS

Extended European Search Report dated Jul. 24, 2023 in European Application No. 20870789.3.
Kawamura M. et al., "Feasibility, Safety, and Therapeutic Efficacy of Human Induced Pluripotent Stem Cell-Derived Cardiomyocyte Sheets in a Porcine Ischemic Cardiomyopathy Model", Circulation, 2012, 126, pp. S29-S37.
Miyagawa S. et al., "Building A New Treatment For Heart Failure-Transplantation of Induced Pluripotent Stem Cell-derived Cells into the Heart", Current Gene Therapy, 2016, vol. 16, No. 1 pp. 5-13.
Takagi D. et al., "Construction of iPS-Derived 3D Tissues with Automatic Coating and Evaluation Technology", Ricoh Technical Report, 2016 No. 41, pp. 118-127.
Li J. et al., "Human Pluripotent Stem Cell-Derived Cardiac Tissue-like Constructs for Repairing the Infarcted Myocardium", Stem Cell Reports, 2017, vol. 9, 14 pages.
Nakane T. et al., "Impact of Cell Composition and Geometry on Human Induced Pluripotent Stem Cells-Derived Engineered Cardiac Tissue", Scientific Reports, 2017, 7:45641, 13 pages.
Gao L. et al., "Large Cardiac Muscle Patches Engineered From Human Induced-Pluripotent Stem Cell-Derived Cardiac Cells Improve Recovery From Myocardial Infarction in Swine", Circulation, 2018, 137, pp. 1712-1730.
Shadrin IY. et al., "Cardiopatch platform enables maturation and scale-up of human pluripotent stem cell-derived engineered heart tissues", Nature Communications, 2017, 8:1825, 15 pages.
International Search Report of PCT/JP2020/034096 dated Nov. 24, 2020 [PCT/ISA/210].

* cited by examiner

[Fig. 1]
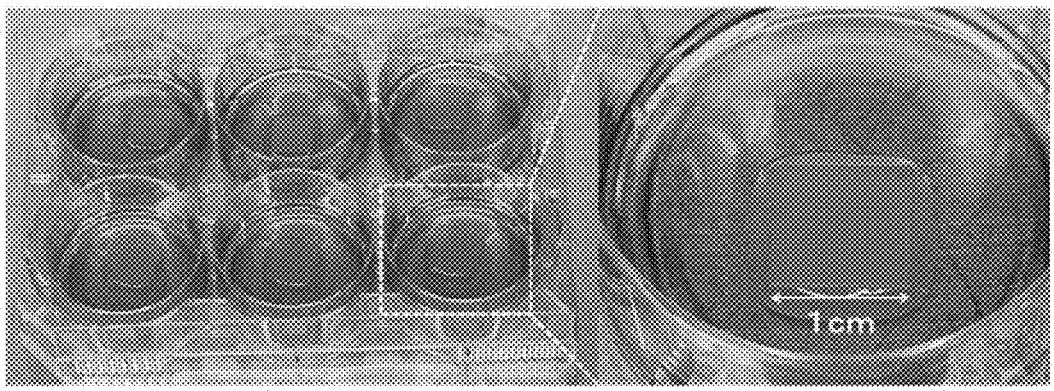
[Fig. 2]
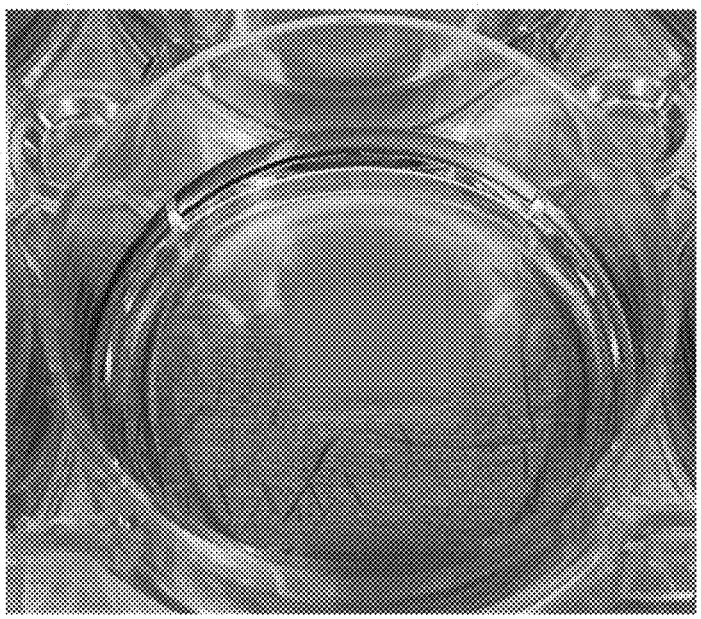

[Fig. 3]
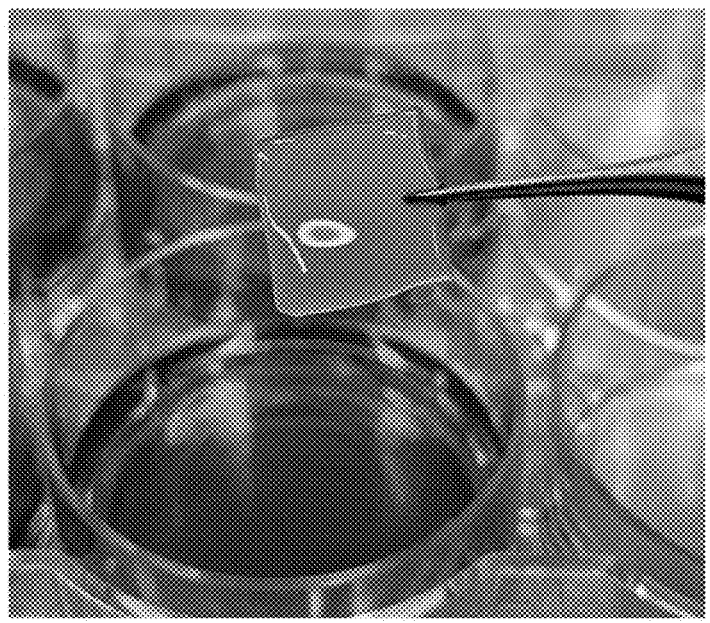
[Fig. 4]
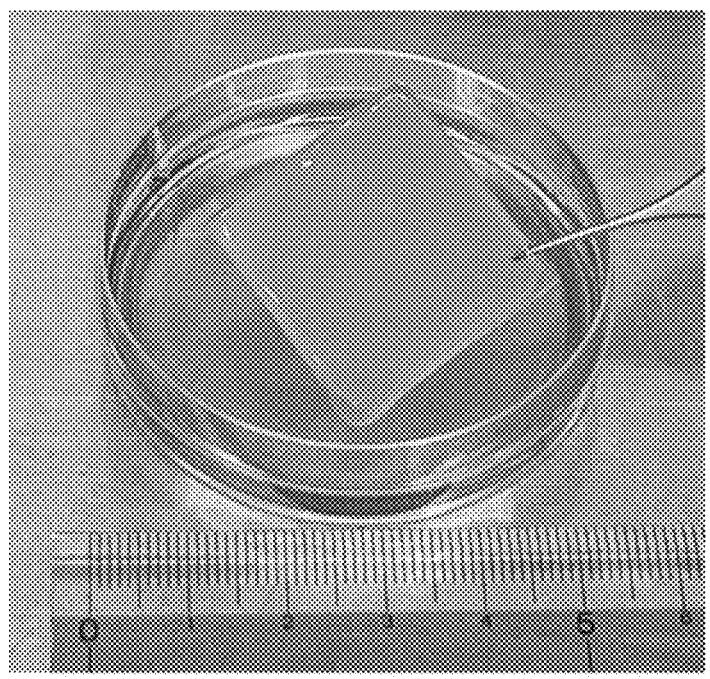

[Fig. 5]
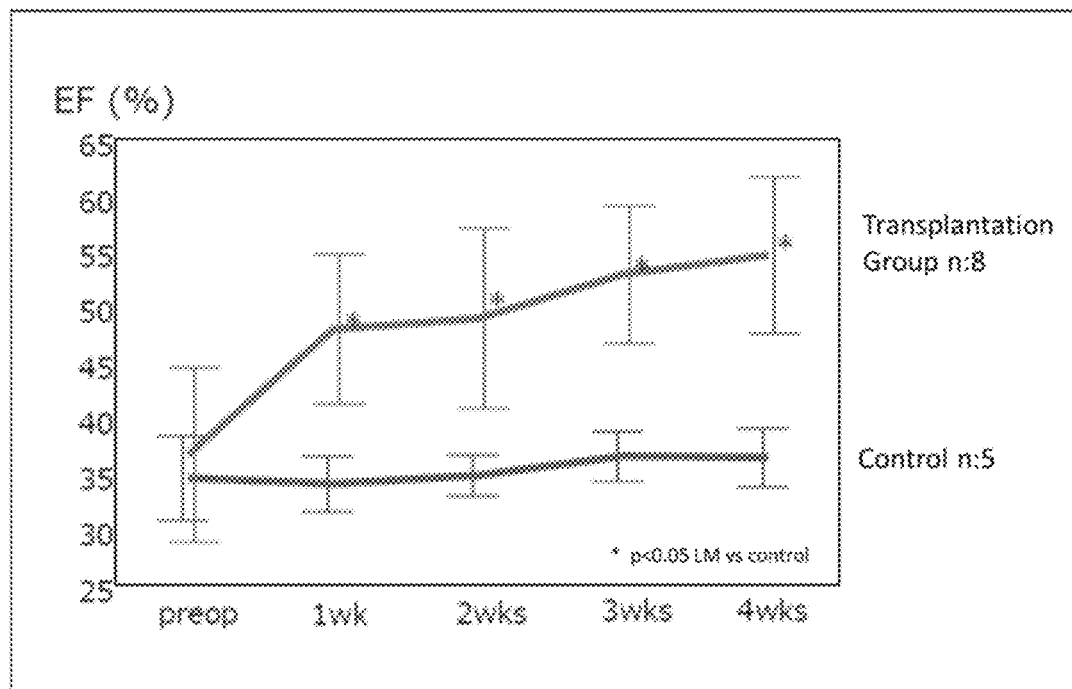
[Fig. 6]
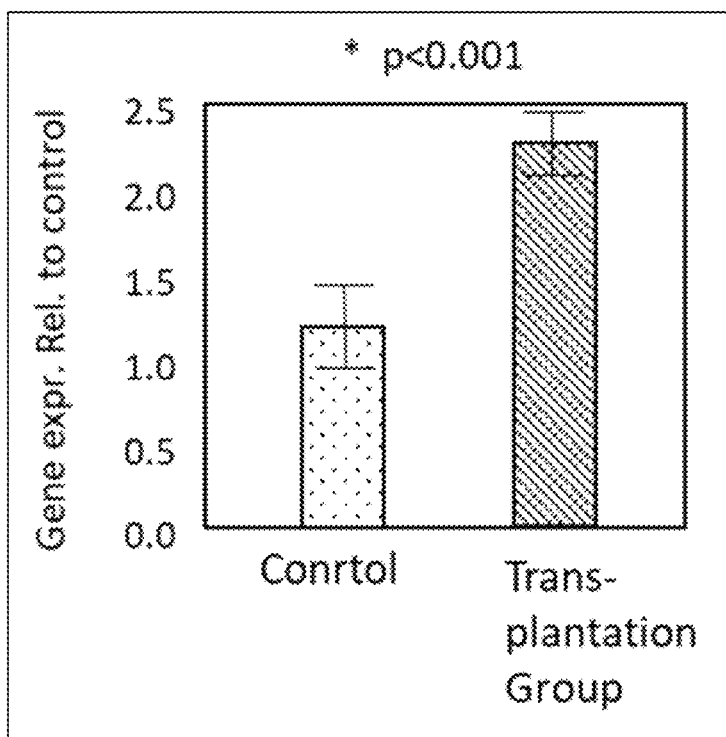

METHOD FOR PRODUCING FIBRIN SHEET

CROSS REFERENCE TO RELATED APPLICATIONS

This application is a National Stage of International Application No. PCT/JP2020/034096, filed Sep. 9, 2020, claiming priority based on Japanese Patent Application No. 2019-181395, filed Oct. 1, 2019.

TECHNICAL FIELD

The present invention relates to a fibrin sheet, and more specifically, to a method for producing a fibrin sheet containing at least one selected from the group consisting of cells and drugs in a fibrin gel.

BACKGROUND ART

In the field of regenerative medicine, there are growing expectations for treatment methods in which a three-dimensional tissue or organ is constructed from cells and then transplanted, from the viewpoint of complementing a lost function of an organ (for example, Kawamura M. et al., Circulation, 2012; 126: S29-37 (NPL 1), Miyagawa S. et al., Current Gene Therapy, 2016, Vol. 16, No. 1, p. 5-13 (NPL 2)). In constructing a three-dimensional tissue or organ, it is necessary to fabricate a tissue containing a sufficient amount of cells extending over several layers to obtain, for example, a better therapeutic effect. To this end, the following methods and the like have been studied in recent years: the Layer by Layer method (LbL method) in which cells are stacked by using a 3D printer (for example, Takagi D. et al., Ricoh Technical Report, 2016, No. 41, p. 118-127 (NPL 3)); a method in which nanofibers are fabricated and cells are seeded on the nanofibers (for example, Li J. et al., Stem Cell Reports, 2017, Vol. 9, 1-14, p. 1546-1559 (NPL 4)); and methods in which a special mold is fabricated and a bioaffinity material and cells are seeded in the mold (Nakane T. et al., Scientific Report, 2017, 7: 45641 (NPL 5), Gao L. et al., Circulation, 2018; 137: 1712-1730 (NPL 6), Shadrin I Y. et al., Nature Communications, 2017; 8: 1825 (NPL 7)).

However, the above-described LbL method requires a special 3D printer capable of seeding cells, the above-described method using nanofibers requires a device that fabricates the nanofibers and a period of time for sufficient engraftment of the cells after seeding, and the above-described method using the special mold requires fabrication of the special mold and a period of time for which the cells are cultured in the mold. Accordingly, these already-existing methods have a problem of requiring a special and expensive device or a long period of time.

In the field of regenerative medicine, cell replacement therapy has also been known in which a cell sheet containing cells is used at a site of a lesion or a site of loss to regenerate tissue. Moreover, studies have been conducted on the use of the above-described three-dimensional tissue or organ constructed by three-dimensionally stacking the cell sheet, for transplantation, drug discovery research, or the like. In this connection, it has been known in the field of surgery that a sheet made of a bioaffinity material is used for prosthesis or reinforcement at an incision site or a site of tissue loss where a lesion has been removed, and it has been also known that the sheet is used as a drug sheet by further adding a drug for treatment to the sheet. Fibrin, collagen, polylactic acid, and the like have been widely used for a substrate (scaffold) of such cell sheets and drug sheets and as the bioaffinity material. Especially, a fibrin gel made of fibrin is advantageous in that the fibrin gel also functions as a bioadhesive because of its tissue conglutination properties. However, since the fibrin gel is paste-like, the fibrin concentration may be increased to make handling thereof relatively easy. This makes it difficult for the contained cells to survive in the fibrin gel. On the other hand, when the fibrin is diluted to a concentration which allows the cells to survive, the fibrin gel becomes difficult to handle, because it is difficult to maintain the shape of the gel. Moreover, because of its strong adhesiveness, the fibrin gel has problems in that cells may be damaged during collection of the cell sheet and that it is difficult to produce and maintain a cell sheet uniformly in any shape. Moreover, presumably, the mainstream of the production of cell sheets, drug sheets, and the like in the future would be automated production using devices. Hence, it is expected that there would be a need for an easier and more convenient production method, from the viewpoints of improvement in maintainability of such devices, size-reduction of such devices, and the like.

CITATION LIST

Non Patent Literature

[NPL 1] Kawamura M. et al., Circulation, 2012; 126: S29-37
[NPL 2] Miyagawa S. et al., Current Gene Therapy, 2016, Vol. 16, No. 1, p. 5-13
[NPL 3] Takagi D. et al., Ricoh Technical Report, 2016, No. 41, p. 118-127
[NPL 4] Li J. et al., Stem Cell Reports, 2017, Vol. 9, 1-14, p. 1546-1559
[NPL 5] Nakane T. et al., Scientific Report, 2017, 7: 45641
[NPL 6] Gao L. et al., Circulation, 2018; 137: 1712-1730
[NPL 7] Shadrin I Y. et al., Nature Communications, 2017; 8: 1825

SUMMARY OF INVENTION

Technical Problem

The present invention has been made in view of the problems of the above-described conventional techniques, and an object of the present invention is to provide a method for producing a fibrin sheet containing at least one selected from the group consisting of cells and drugs in a fibrin gel, the method enabling the fibrin sheet to be produced uniformly in any shape and in an easy and convenient manner, while reducing damage on the cells and drugs, even when the fibrin concentration is low enough for the cells to survive.

Solution to Problem

To achieve the above-described object, the present inventors have conducted intensive study on a method for producing a fibrin sheet containing at least one selected from the group consisting of cells and drugs in a fibrin gel. As a result, the present inventors have found the following fact. Specifically, a fibrinogen solution containing the cells and/or drug and fibrinogen is applied dropwise onto a surface of a substrate made of a gelatin hydrogel; subsequently, a fibrin precursor liquid is prepared by adding thrombin to the fibrinogen solution on the surface of the substrate; and a support film is placed on and in contact with a top surface of the fibrin precursor liquid. In such a case, the fibrin precursor liquid can be spread between uniform surfaces of the substrate and the support film by surface tension without using any operation which may mechanically damage the cells, such as spreading using an applicator, and the fibrin sheet can be formed uniformly by a reaction between the fibrinogen and the thrombin. Moreover, the present inventors have found that when the substrate is melted at a temperature not lower than a melting temperature of the gelatin hydrogel after formation of the fibrin sheet, the fibrin sheet and the substrate can be easily separated from each other, irrespective of the fibrin concentration in the fibrin sheet and even when the concentration is low enough for cells to survive. Moreover, the present inventors have found that the fibrin sheet can easily be obtained in any shape by adjusting the shape of the support film. These findings have led to the completion of the present invention.

Specifically, the present invention includes the following aspects.

[1] A method for producing a fibrin sheet containing at least one selected from the group consisting of cells and drugs in a fibrin gel, the method comprising:
  a step 1 of applying a fibrinogen solution containing at least one selected from the group consisting of cells and drugs and fibrinogen dropwise onto a surface of a substrate made of a gelatin hydrogel;
  a step 2 of adding thrombin to the fibrinogen solution on the surface of the substrate:
  a step 3 of placing a support film on and in contact with a top surface of the fibrinogen solution to which the thrombin has been added;
  a step 4 of forming a fibrin sheet containing the at least one selected from the group consisting of cells and drugs in a fibrin gel between the substrate and the support film by a reaction between the fibrinogen and the thrombin; and
  a step 5 of melting the substrate at a temperature not lower than a melting temperature of the gelatin hydrogel to separate, from the substrate, the fibrin sheet supported by the support film.

[2] The method for producing a fibrin sheet according to [1], wherein
  the fibrin sheet is a cell sheet containing at least a cell in the fibrin gel, and
  the substrate is a cell culture substrate.

[3] The method for producing a fibrin sheet according to claim [1] or [2], further comprising, prior to the step 1, a step of heating an aqueous gelatin solution containing gelatin and water and then cooling the aqueous gelatin solution to obtain the gelatin hydrogel.

[4] The method for producing a fibrin sheet according to any one of [1] to [3], wherein
  the support film is a polypropylene sheet.

[5] The method for producing a fibrin sheet according to any one of [1] to [4], wherein
  the substrate is melted at 30 to 40° C. in the step 5.

Advantageous Effects of Invention

According to the present invention, it is possible to provide a method for producing a fibrin sheet containing at least one selected from the group consisting of cells and drugs in a fibrin gel, the method enabling the fibrin sheet to be produced uniformly in any shape and in an easy and convenient manner, while reducing damage on the cells and drugs, even when the fibrin concentration is low enough for the cells to survive.

Moreover, the use of the fibrin sheets (cell sheets and/or drug sheet) obtained according to the present invention and stacking thereof or the like make it possible to construct a three-dimensional biomaterial, such as a three-dimensional tissue or organ, in an easy and convenient manner and in a short period of time. The fibrin sheet and the three-dimensional biomaterial can be used for cell replacement therapy or treatment of chronic diseases and acute diseases and can also be used for elucidation of biochemical phenomena and for cell culture intended for production of useful substances.

BRIEF DESCRIPTION OF DRAWINGS

FIG. 1 is a photograph showing forms of a substrate, a fibrin sheet, and a support film in step 4 of Example 1.

FIG. 2 is a photograph showing forms of a melted substrate, the fibrin sheet, and the support film in step 5 of Example 1.

FIG. 3 is a photograph showing a form of a fibrin sheet obtained in Example 1.

FIG. 4 is a photograph showing a form of a fibrin sheet obtained with a larger area.

FIG. 5 is a graph showing the results of cardiac function evaluation for evaluation of the fibrin sheet obtained in Example 1.

FIG. 6 is a graph showing the measurement results of the amount of expression of the VEGF gene for evaluation of the fibrin sheet obtained in Example 1.

DESCRIPTION OF EMBODIMENTS

Hereinafter, the present invention will be described in detail based on preferred embodiments thereof; however, the following embodiments are provided as examples for describing the present invention, and are not intended to limit the present invention to the following contents. The present invention can be carried out while being modified, as appropriate, within the gist of the present invention.

A method for producing a fibrin sheet of the present invention is a method for producing a fibrin sheet containing at least one selected from the group consisting of cells and drugs in a fibrin gel, the method comprising:
  a step 1 of applying a fibrinogen solution containing at least one selected from the group consisting of cells and drugs and fibrinogen dropwise onto a surface of a substrate made of a gelatin hydrogel;
  a step 2 of adding thrombin to the fibrinogen solution on the surface of the substrate;
  a step 3 of placing a support film on and in contact with a top surface of the fibrinogen solution to which the thrombin has been added;
  a step 4 of forming a fibrin sheet containing the at least one selected from the group consisting of cells and drugs in a fibrin gel between the substrate and the support film by a reaction between the fibrinogen and the thrombin; and
  a step 5 of melting the substrate at a temperature not lower than a melting temperature of the gelatin hydrogel to separate, from the substrate, the fibrin sheet supported by the support film.

(Fibrin Sheet)

In the present invention, the "fibrin sheet" refers to a sheet comprising a fibrin gel and at least one selected from the group consisting of cells and drugs contained in the fibrin gel. In the present invention, the "fibrin gel" refers to a polymer formed by a reaction between fibrinogen and thrombin. The fibrin gel mainly has a function of causing cells to adhere to each other.

The fibrinogen is a protein in the blood, and fibrinogen obtained from the plasma of human or an animal other than human can be used usually. From the viewpoint of biocompatibility, it is desirable to use, as a raw material, fibrinogen obtained from the plasma of human for a case where the fibrin sheet is used for human, or fibrinogen obtained from the plasma of an animal other than human for a case where the fibrin sheet is used for the animal. The fibrinogen may be, for example, dry human fibrinogen produced according to The Minimum Requirements for Biological Products (June 2019) issued by Ministry of Health, Labour and Welfare of Japan, and commercially available fibrinogen may also be used, as appropriate.

The above-described thrombin is an enzyme that catalyzes a reaction of the fibrinogen into fibrin, and ordinally, thrombin obtained from the plasma of human or an animal other than human can be used. The thrombin may be, for example, one prepared by treating prothrombin obtained by purification from the plasma of human or cattle with thromboplastin, snake venom, or the like in the presence of $Ca^{2+}$, and commercially available thrombin may also be used, as appropriate.

Fibrin sheets according to the present invention include a cell sheet containing cells in the fibrin gel, a drug sheet containing a drug in the fibrin gel, and a cell•drug sheet containing cells and a drug in the fibrin gel (in the present description, these are collectively referred to as "cell sheet and/or drug sheet" in some cases).

In the present invention, the cells contained in the fibrin gel are not particularly limited, as long as the cells can be used for cell transplantation. The cells can be selected, as appropriate, according to the purpose, and may be any of master cells, somatic stem cells, progenitor cells, and mature cells. The cells may be of only one of these types or a combination of two or more types.

Examples of the master cells include ES cells, GS cells, and iPS cells. Examples of the somatic stem cells include mesenchymal stem cells (MSC), hematopoietic stem cells, amniocytes, umbilical cord blood cells, bone marrow-derived cells, cardiac stem cells, adipose-derived stem cells, and neural stem cells. Examples of the progenitor cells and the mature cells include chondrocytes, chondroprogenitor cells, synovium-derived cells, adipose-derived cells, cardiomyocytes, and vascular endothelial cells. The cells may also be cells derived from the above-described master cells, somatic stem cells, or progenitor cells (for example, iPS cell-derived cells (cardiomyocytes, vascular endothelial cells), or the like). Sources from which the above-described cells may be derived include human, and mammals other than human (primates such as chimpanzees and monkeys; domestic animals or companion animals such as cattle, pigs, horses, chickens, cats, and dogs), birds, reptiles, amphibians, and fishes, and the cells may be autologous cells whose origin is the subject to which the fibrin sheet is to be transplanted or allogeneic cells whose origin is other than the subject to which the fibrin sheet is to be transplanted.

When the fibrin sheet is the cell sheet or the cell•drug sheet, the amount of cells (when the cells are of two types or more, the total amount of the two or more types of cells) contained in the fibrin gel is preferably such that the number of the cells is $1\times10^6$ to $1\times10^7$ per a volume of 100 μL of the fibrin sheet. Note that, in addition to the cells (cells of interest), the fibrin gel may contain cells introduced as contaminants during separation or the like.

In the present invention, examples of the drug contained in the fibrin gel include low molecular weight drugs such as antitumor agents (alkylating drugs, platinum compounds, antimetabolites, topoisomerase inhibitors, anticancer antibiotics, microtubule-acting anticancer agents, and the like), antibacterial agents (penicillins, cephems, carbapenems, aminoglycosides, quinolones, macrolides, tetracyclines, glycopeptides, and the like), antiinflammatories (steroids, NSAIDs, and the like), antiviral agents, and hormones; bioactive peptides such as bone morphogenic proteins and bone growth factors; proteins; glycoproteins; polysaccharides; nucleic acids; nutrients (citric acid and the like); vitamins: and opioids, and one of these drugs alone or a combination of two or more thereof may be contained.

When the fibrin sheet is the drug sheet or the cell•drug sheet, the amount of the drug (when two or more drugs are contained, the total amount of the two or more drugs) contained in the fibrin gel cannot be generalized, because the amount is adjusted, as appropriate, according to the purpose of use thereof or the like. For example, the amount of the drug is preferably 1 to 40% by mass, more preferably 1 to 30% by mass, and further preferably 1 to 20% by mass, relative to the total amount of the fibrin sheet.

The fibrin sheet according to the present invention may further comprise additional components, in addition to the fibrin gel, the cells, and the drug. The additional components include components derived from solvents of a fibrinogen solution or a thrombin solution described below, specifically, components derived from solvents such as injectable physiological saline, buffer solutions (phosphate buffers such as PBS, citrate buffers, and the like), cell culture media (DMEM and the like); components added to the fibrinogen solution or thrombin solution described below, specifically, solubilizers such as surfactants, serum albumin (human serum albumin or the like), sugars, sugar alcohols, amino acids (arginine, isoleucine, glutamic acid, and the like) or salts thereof, sodium citrate, sodium chloride, and the like. In addition, when the fibrin sheet is the cell sheet or the cell•drug sheet, the additional components include proteins and glycoproteins constituting an extracellular matrix (laminins (for example, laminin-221) and the like), and cell growth factors. One of these components alone or a combination of two or more thereof may be contained as the additional component. The composition and content of these additional components can be adjusted, as appropriate, according to the cells or drug to be contained in the fibrin sheet, the types of the additional components, the purpose of use of the fibrin sheet, or the like.

Although the thickness of the fibrin sheet according to the present invention is not particularly limited, the fibrin sheet preferably has a thickness which correspond to, for example, about 100 to 300 μL/1 $cm^2$, and the thickness is more preferably in a range of 1 to 3 mm. However, a three-dimensional biomaterial with a desired thickness can be formed from the fibrin sheet according to the present invention by stacking thereof. In the present invention, the area of the fibrin sheet is not particularly limited, either, and can be adjusted, as appropriate, according to the purpose of use or the like.

(Step 1)

In the method for producing a fibrin sheet of the present invention, first, a fibrinogen solution containing at least one selected from the group consisting of cells and drugs and fibrinogen is applied dropwise onto a surface of a substrate made of a gelatin hydrogel (step 1).

The substrate according to the present invention is made of a gelatin hydrogel. In the present invention, the "gelatin hydrogel" is a gel containing at least gelatin and water, and one in which cross-linking is formed between molecules of the gelatin.

The "gelatin" according to the present invention is not particularly limited, as long as the gelatin is cross-linkable. The gelatin may be a natural gelatin produced from skin, bone, ligament, tendon, or the like of an animal such as cattle, a pig, a whale, a fish, or the like, or may be a polypeptide or protein-like substance (recombinant gelatin) made by a gene recombination technique and having an amino acid sequence similar to gelatin. In addition, the natural gelatin may be type-A gelatin (isoelectric point: 8 to 9) derived from what is called acid-cured tissue, or may be type-B gelatin (isoelectric point: 4.8 to 5.0) derived from what is called lime-cured tissue. Commercially available one can be used, as appropriate, as the gelatin.

In the gelatin hydrogel, the cross-linking between molecules of the gelatin can also be conducted by a chemical approach using a cross-linking agent or the like or a physical approach using ultraviolet rays or the like. However, the gelatin hydrogel according to the present invention is preferably one obtained by forming the cross-linking between molecules of the gelatin using a method (heat treatment method) in which an aqueous gelatin solution containing gelatin and water is heated and then cooled, from the viewpoint of resolubility upon heating or from the viewpoint of uniformity of the surface of the substrate.

The aqueous gelatin solution may be, for example, one obtained by adding gelatin to an aqueous solvent. A solvent containing at least water can be used as the aqueous solvent, and examples thereof include injectable distilled water, injectable physiological saline, buffer solutions (phosphate buffers such as PBS, citrate buffers, and the like), and cell culture media (DMEM and the like), and one of these solvents alone or a combination of two or more thereof may be used. Of these solvents, a cell culture medium suitable for cells to be contained is preferably contained as the aqueous solvent when the fibrin sheet according to the present invention is the cell sheet or the cell•drug sheet, and the substrate is more preferably a substrate containing at least gelatin and the cell culture medium, i.e., a cell culture substrate.

The concentration of gelatin in the aqueous gelatin solution is preferably 1 to 12% by mass, more preferably 2 to 10% by mass, and further preferably 3 to 8% by mass.

Conditions under which the gelatin hydrogel is prepared by the heat treatment method are preferably, for example, such that the aqueous gelatin solution is heated at 30 to 40° C., preferably at 35 to 40° C. for 5 to 40 minutes, preferably for 10 to 30 minutes, and then cooled at 0 to 20° C., preferably at 4 to 10° C. for 5 to 120 minutes, preferably for 10 to 60 minutes. The heating method may be, for example, a method using a water bath or an incubator, and the cooling method may be a method of being allowed to stand in a room temperature (about 25° C.) environment or in a cold place.

The gelatin hydrogel can be obtained on an apparatus such as a Petri dish, a multi-well plate, a flask, or a microcarrier by placing the heated aqueous gelatin solution into the apparatus followed by cooling. As the substrate according to the present invention, it is preferable to directly use the gelatin hydrogel on such an apparatus from the viewpoint of ease of handling. However, the gelatin hydrogel may be used after detachment from the apparatus, or after being cut into pieces having a desired size, as appropriate.

The fibrinogen solution according to the present invention contains at least one selected from the group consisting of cells and drugs and fibrinogen. The cells, the drug, and the fibrinogen, including preferred modes thereof, are as described above.

The amounts of the cells and the drug contained in the fibrinogen solution are each preferably adjusted, as appropriate, to make the amount thereof in the obtained fibrin sheet fall within the preferred range of the amount contained.

The amount of fibrinogen contained in the fibrinogen solution is preferably 0.4 to 2% by mass, and more preferably 0.4 to 1% by mass, in terms of protein content. If the amount of fibrinogen contained is less than the lower limit, it tends to be difficult to form the fibrin gel. Meanwhile, if amount of fibrinogen contained exceeds the upper limit, the fibrin concentration in the fibrin gel is so high that it tends to be difficult for cells contained therein to survive.

As the solvent for the fibrinogen solution, a solvent commonly used as a solvent for melting fibrinogen can be used, and examples thereof include aqueous solvents such as injectable distilled water, injectable physiological saline, buffer solutions with a pH of 5 to 8 (phosphate buffers such as PBS, citrate buffers, and the like), and cell culture media (such as DMEM). One of these solvents alone or a combination of two or more thereof may be used as the solvent. Of these solvents, a cell culture medium suitable for cells to be contained in the fibrin sheet is preferably contained as the solvent, when the fibrin sheet is the cell sheet or the cell•drug sheet.

In addition to the cells, the drug, and the fibrinogen, the fibrinogen solution may further contain additive components such as solubilizers (surfactants and the like), serum albumin (human serum albumin and the like), sugars, sugar alcohols, amino acids (arginine, isoleucine, glutamic acid, and the like) or salts thereof, sodium citrate, sodium chloride, proteins and glycoproteins constituting extracellular matrices (laminins and the like), and cell growth factors, unless an effect of the invention is impaired.

A method for applying the fibrinogen solution dropwise onto a surface of the substrate is not particularly limited, and examples thereof include a dropwise application method using a pipettor and a dropwise application method using a syringe. The amount of the fibrinogen solution applied dropwise is preferably 60 to 180 μL, more preferably 80 to 160 μL, and further preferably 100 to 140 μL, from the viewpoint of uniformity of the obtained fibrin sheet.

(Step 2)

In the method for producing a fibrin sheet of the present invention, thrombin is added to the fibrinogen solution on the surface of the substrate (step 2) after the step 1. The thrombin, including preferred modes thereof, is as described above.

The amount of thrombin added relative to the fibrinogen solution is preferably 0.75 to 375 units (U) relative to 100 mg of fibrinogen (in terms of protein content). If the amount of thrombin added is less than the lower limit, it tends to be difficult to form a fibrin gel. Meanwhile, if the amount of thrombin added exceeds the upper limit, the fibrin concentration in the fibrin gel is so high that it tends to be difficult for cells contained therein to survive. Note that the "thrombin quantification method" in The Japanese Pharmacopoeia can be used with necessary modifications as a thrombin quantification method in the present invention.

In the present invention, the thrombin may be added in the form of a thrombin solution containing thrombin. A solvent commonly used can be used as a solvent for the thrombin solution, and examples thereof include aqueous solvents such as injectable distilled water, injectable physiological saline, buffer solutions with a pH of 5 to 8 (phosphate buffers such as PBS, citrate buffers, and the like), and cell culture media (such as DMEM). One of these solvents alone or a combination of two or more thereof may be used. Of these solvents, a cell culture medium suitable for cells to be contained is preferably contained as the solvent, when the fibrin sheet is the cell sheet or the cell•drug sheet.

In addition to thrombin, the thrombin solution may further contain additive components such as solubilizers (surfactants and the like), serum albumin (human serum albumin and the like), sugars, sugar alcohols, amino acids (arginine, isoleucine, glutamic acid, and the like) or salts thereof, sodium citrate, sodium chloride, proteins and glycoproteins constituting extracellular matrices (laminins and the like), and cell growth factors, unless an effect of the invention is impaired.

A method for adding thrombin to the fibrinogen solution is not particularly limited, and examples thereof include a method in which the thrombin solution is added to the fibrinogen solution (preferably a drop of the fibrinogen solution) using a pipettor, a method in which the thrombin solution is attached to a bottom surface of a support film to be described below and then placed on a top surface of the fibrinogen solution, and a method in which these methods are combined. Here, the amount of the thrombin solution added is preferably 1 to 25 μL, more preferably 2 to 20 μL, and further preferably 2 to 15 μL, from the viewpoint of uniformity of the obtained fibrin sheet.

In the step 2, the fibrinogen solution and the thrombin may be stirred by pipetting or the like. However, the fibrinogen solution to which the thrombin has been added (sometimes referred to as "fibrin precursor liquid" herein) is preferably kept in a state where a drop is formed on the substrate. In the present invention, the "drop" preferably do not cover all over the surface of the substrate, and the ratio of the volume (μL) of the drop to the contact area (mm$^2$) with the substrate is 0.5 μL/mm$^2$ or higher, and more preferably 1 μL/mm$^2$ or higher.

(Step 3)

In the method for producing a fibrin sheet of the present invention, a support film is placed on and in contact with a top surface of the fibrinogen solution to which the thrombin has been added (step 3). In the step 3, only placing the support film on and in contact with a top surface of the fibrin precursor liquid (preferably a drop of the fibrin precursor liquid) enables the fibrin precursor liquid to be uniformly spread owing to the own weight of the support film and the surface tension between the drop of the fibrin precursor liquid and the support film, and also makes it possible to bring the obtained fibrin sheet and the support film into close contact with each other. When the step 3 is conducted after the step 2, the formation of the fibrin sheet in the step 4 to be described below simultaneously proceeds after the step 2. For this reason, it is preferable in the step 3 to place the support film on the top surface of the fibrin precursor liquid immediately after the addition of thrombin to the fibrinogen solution, preferably within 5 minutes after the addition, and more preferably within 2 minutes after the addition. In addition, the step 2 (the addition of thrombin to the fibrinogen solution) and the step 3 may be conducted simultaneously, and the step 2 and the step 3 can be conducted simultaneously, for example, by attaching the thrombin solution to the bottom surface of the support film (preferably applying dropwise and spreading the thrombin solution) and then placing the support film on the top surface of the fibrinogen solution (preferably a drop of the fibrin solution) or other methods.

In the present invention, the "support film" is not particularly limited, as long as the support film can support the obtained fibrin sheet and retain the shape of the fibrin sheet. However, the support film is preferably easily detachable from the fibrin sheet before use of the fibrin sheet, and also preferably has a uniform surface with less concavities and convexities as the surface to be in contact with the fibrin precursor liquid. Examples of the support film include a polypropylene sheet, polyethylene, paper, a metal such as titanium or aluminum, glass, and a combination of two or more thereof. Of these examples, a polypropylene sheet is preferable as the support film, from the viewpoints of the uniformity of the surface, ease of handling, and ease of detachment from the fibrin sheet.

In addition, the support film has a weight per unit area of preferably 0.01 to 0.2 g/cm$^2$, more preferably 0.01 to 0.1 g/cm$^2$, and further preferably 0.01 to 0.05 g/cm$^2$, from the viewpoint that the fibrin sheet with a preferred thickness is obtained owing to the own weight of the support film.

Regarding the area of the support film, the area of the surface of the support film to be in contact with the fibrin precursor liquid is preferably 50 to 200 mm$^2$, more preferably 50 to 150 mm$^2$, and further preferably 75 to 100 mm$^2$ relative to 100 μL of the amount of the solution. The shape of the support film is not particularly limited, and any shape can be selected such as a circular shape, an oval shape, a polygonal shape such as a square or rectangular shape, a shape with a hole, a shape in which cuts are provided on a surface opposite to the surface to be in contact with the fibrin sheet to allow bending, and the like. The use of a support film having a shape in which cuts are provided on the surface opposite to the surface to be in contact with the fibrin sheet enables the fibrin sheet to be folded up, and makes it possible to, for example, transplant a fibrin sheet having a larger area with a microincision. Moreover, the thickness of the support film is not particularly limited, and is preferably 0.05 to 0.4 μm, from the viewpoint of ease of handling.

(Step 4)

In the method for producing a fibrin sheet of the present invention, a fibrin sheet containing the at least one selected from the group consisting of cells and drugs in a fibrin gel is formed between the substrate and the support film by a reaction between the fibrinogen and the thrombin (step 4). The fibrin sheet, and the cells, the drug, the fibrin gel, and the optional additional components contained in the fibrin sheet are each as described above, including preferred mode thereof. In the present invention, since the fibrin sheet starts to be formed in the step 2, part of the step 4 may be conducted simultaneously with the step 2 and/or the step 3.

The conditions for the reaction between the fibrinogen and the thrombin in the step 4 are preferably such that the fibrinogen and the thrombin are allowed to stand, for example, 4 to 25° C., preferably 4 to 20° C., for 5 to 20 minutes, preferably for 5 to 15 minutes. The fibrin gel is formed by reacting the fibrinogen and the thrombin with each other, and such a step 4 makes it possible to obtain the fibrin sheet between the substrate and the support film.

(Step 5)

In the method for producing a fibrin sheet of the present invention, the substrate is melted at a temperature not lower than a melting temperature of the gelatin hydrogel, to separate, from the substrate, the fibrin sheet supported by the support film (step 5) after the step 4.

The temperature at which the substrate is melted in the step 5 may be any temperature not lower than a melting temperature of the gelatin hydrogel, i.e., any temperature not lower than the melting temperature after setting of the gelatin constituting the gelatin hydrogel. Specifically, the temperature at which the substrate is melted is preferably 30 to 40° C., and more preferably 35 to 40° C., from the viewpoints of reducing cell killing and drug inactivation and the viewpoint of further facilitating the separation of the fibrin sheet and the substrate from each other. In addition, the time for which the substrate is melted at the above-described temperature is not particularly limited, and, for example, is preferably 10 to 60 minutes, and more preferably 10 to 30 minutes.

A method for melting the substrate in the step 5 is not particularly limited, and may be, for example, a method in which the substrate, the fibrin sheet, and the support film after the step 4 are allowed to stand on a water bath or in an incubator under the above-described conditions. In the step 5 as described above, the gelatin hydrogel constituting the substrate is melted, and the adhesion between the fibrin sheet and the surface of the substrate is eliminated. Hence, collecting the support film enables collection of the fibrin sheet stacked and supported on the support film.

According to the present invention, a fibrin sheet can be produced in an easy and convenient manner, even when the fibrin concentration is low enough for cells to survive. Hence, when the fibrin sheet is the cell sheet or the cell•drug sheet, cells can be contained in the fibrin sheet, while being kept alive. In addition, since the cells can be moved in the fibrin sheet having a low fibrin concentration, it is possible to obtain a fibrin sheet in which the cells are three-dimensionally dispersed or a fibrin sheet in which the cells are accumulated in a surface layer of the sheet, according to the present invention.

The fibrin sheet obtained according to the present invention can directly be used as a cell sheet and/or a drug sheet, and can be used preferably for treatment of a disease by cell transplantation (cell replacement therapy) or for prosthesis and reinforcement in a site where an incision has been made during surgery or a site of tissue loss where a lesion has been removed. In addition, the fibrin sheet obtained according to the present invention can be formed into a three-dimensional biomaterial by stacking thereof, which can also be used for transplantation, drug discovery research, or the like.

As an example of a treatment method using the fibrin sheet obtained according to the present invention, a method for treating a cardiac disease based on cell transplantation using a cell sheet obtained by the production method of the present invention is described below. In addition to cardiac diseases, the treatment method using a fibrin sheet obtained according to the present invention may be applied to, for example, treatment of liver hypofunction such as hepatic cirrhosis and viral hepatitis, gastrointestinal ulcer, gastrointestinal perforation, epithelial ulcer, epithelial defect, corneal injury, and hemostasis at bleeding sites associated with vascular injury or organ injury, from the viewpoints of cell replacement in or reinforcement of a lost tissue or a hypoactive organ.

The "cardiac disease" to which the treatment method is applied may be, for example, a disease selected from the group consisting of heart failure, ischemic heart disease, myocardial infarction, cardiomyopathy, myocarditis, hypertrophic cardiomyopathy, the dilated phase of hypertrophic cardiomyopathy, and dilated cardiomyopathy.

The method for treating a cardiac disease can be applied to a human subject and a subject other than human. Organisms to which the method can be applied are not particularly limited, as long as the organisms have the target of the treatment, i.e., heart. Examples of the organisms include human, mammals other than human, birds, reptiles, amphibians, and fishes. The mammals other than human include, but are not limited to, primates such as chimpanzee and monkeys, as well as domestic animals and companion animal such as cattle, pigs, horses, chickens, cats, and dogs. As the cells contained in the cell sheet, cells obtained from a source compatible with an organism to which the treatment is to be applied may be used, and the cells are preferably allogeneic cells, and particularly preferably autologous cells, from the viewpoints of suppression of rejection and the like.

In the method for treating a cardiac disease, it is preferable to cover the surface of the heart of a subject suffering from a cardiac disease (preferably a lesion (for example, a myocardial infarction lesion)) with the cell sheet. For transplantation of the cell sheet to the surface of the heart, the cell sheet can easily be fixed by being stuck to the surface of the heart, because the cell sheet is a fibrin sheet.

The method for treating a cardiac disease may be used in combination with an additional treatment, as appropriate. For example, the additional treatment may be coronary artery bypass graft surgery, percutaneous coronary angioplasty, left ventricular plastic surgery, or the like for chronic myocardial infarction or may be coronary artery bypass graft surgery, percutaneous coronary angioplasty, or the like for acute myocardial infarction. Moreover, it is also possible to use the method in combination with valve replacement or pediatric cardiac surgery.

EXAMPLES

Examples of the present invention will be described below; however, the present invention is not limited to these Examples at all.

Example 1

<Materials>
iPS-CMs: human iPS cell-derived cardiomyocytes
DMEM: DMEM High Glucose (nacalai tesque, Code 08458-16),
PBS: D-PBS(–) (nacalai tesque, Code 14249-24),
Gelatin: Gelatin from porcine skin (Sigma, G1890-100G),
Fibrinogen: Beriplast P Combi-set Solution A (CSL Behring, 87799),
Thrombin: Beriplast P Combi-set Solution B (CSL Behring, 87799),
Polypropylene sheet (PP sheet): area: 10 mm×10 mm, thickness: 0.3 μm.

<Production of Fibrin Sheet>
First, 1.6 g of gelatin was added to 40 mL of DMEM and melted for 10 to 20 minutes using a water bath at 37° C. to prepare a 4 w/v % (g/mL %, hereinafter the same) gelatin solution. Subsequently, a gelatin hydrogel was formed by adding 3 mL of the gelatin solution to each well of a 6-well plate followed by cooling at 4° C. for 20 minutes to prepare a substrate made of a gelatin hydrogel. In addition, 120 μL of a fibrinogen solution prepared by mixing 100 μL of iPS-CMs ($5 \times 10^6$ cells) from which foreign substances had been removed with a 70-μm filter and whose concentration had been adjusted by centrifugation, 10 μL of fibrinogen obtained by diluting Beriplast P Solution A 2-fold with DMEM, and 10 μL of PBS with each other was applied dropwise onto a surface of the substrate (approximately 4° C.) immediately after the mixing (step 1). Subsequently, 2 μL of a thrombin solution prepared by diluting Beriplast P Solution B (0.03 U/μL) 10-fold with DMEM was added to the fibrinogen solution on the surface of the substrate (step 2), and immediately thereafter a polypropylene sheet (support film) was placed on and in contact with a top surface of the fibrinogen solution to which the thrombin solution had been added (step 3). This was allowed to stand at 4° C. for 10 minutes, and solidification of the fibrinogen solution to form a fibrin gel (fibrin sheet) was confirmed (step 4). Then, the substrate made of the gelatin hydrogel was melted in an incubator at 37° C. for 20 minutes (step 5), and the fibrin gel (a fibrin sheet containing $5\times10^6$ iPS-CMs in the fibrin gel) was collected together with the polypropylene sheet (step 6). The obtained fibrin sheet had an area of 1 cm$^2$, and a thickness of approximately 1.2 mm. FIG. 1 shows the shapes of the substrate, fibrin sheet, and support film in the step 4, and FIG. 2 shows the shapes of the melted substrate, the fibrin sheet, and the support film in the step 5. Moreover, FIG. 3 shows the shape of the fibrin sheet obtained in the step 6. As shown in FIG. 3, the obtained fibrin sheet was uniform without concavities and convexities. In addition, the cells were accumulated in the surface layer to form a structure with a thickness of 100 to 150 μm in the obtained fibrin sheet.

Moreover, it has been shown that, by increasing the fibrinogen solution and the thrombin solution and also increasing the area of the polypropylene sheet, a fibrin sheet with a larger area was obtained uniformly in the same manner. FIG. 4 shows the shape of the fibrin sheet obtained with a larger area.

<Evaluation of Fibrin Sheet>

Two weeks after myocardial infarction was developed in a nude rat myocardial infarction model, the fibrin sheet was transplanted by being stuck onto a surface of the peri-infarct region of the cardiac muscle. Every week after the transplantation and until Week 4, cardiac functions (contractile performance, end-systolic dimension, and end-diastolic dimension) were evaluated by echocardiography. In addition, the amount of the VEGF (cytokine) gene expressed in the peri-infarct region was measured by qPCR on Week 4 after transplantation.

FIG. 5 shows the results of the evaluation of the cardiac functions in the nude rat myocardial infarction model to which the fibrin sheet was transplanted (transplantation group, n: 8) and the nude rat myocardial infarction model to which the fibrin sheet was not transplanted (Control, n: 5). In FIG. 5, the vertical axis (EF (%)) is the left ventricular ejection fraction. As shown in FIG. 5, significant improvement in the cardiac function was observed in the rats to which the fibrin sheet was transplanted (transplantation group) during 4 weeks after the transplantation.

In addition, FIG. 6 shows the measurement results of the amounts of the VEGF gene expressed in the nude rat myocardial infarction model to which the fibrin sheet was transplanted (transplantation group, n: 8) and in the nude rat myocardial infarction model to which the fibrin sheet was not transplanted (Control, n: 5). In FIG. 6, the vertical axis represents the amount of the VEGF gene expressed relative to the control group. As shown in FIG. 6, an enhanced expression of the VEGF gene, which is a cytokine associated with angiogenesis, was observed in the peri-infarct regions of the rats to which the fibrin sheet was transplanted (transplantation group). In addition, in the transplantation group, the size of the cardiac muscle in the peri-infarct region was significantly small, indicating that hypertrophy of the cardiac muscle was suppressed. Moreover, it was also shown that the angiogenesis was improved.

INDUSTRIAL APPLICABILITY

As described above, according to the present invention, it is possible to provide a method for producing a fibrin sheet containing at least one selected from the group consisting of cells and drugs in a fibrin gel, the method enabling the fibrin sheet to be produced uniformly in any shape and in an easy and convenient manner, while reducing damage on the cells and the drug, even when the fibrin concentration is low enough for the cells to survive.

The invention claimed is:

1. A method for producing a fibrin sheet containing at least one selected from the group consisting of cells and drugs in a fibrin gel, the method comprising:
   a step 1 of applying a fibrinogen solution containing at least one selected from the group consisting of cells and drugs and fibrinogen dropwise onto a surface of a substrate made of a gelatin hydrogel;
   a step 2 of adding thrombin to the fibrinogen solution on the surface of the substrate;
   a step 3 of placing a support film on and in contact with a top surface of the fibrinogen solution to which the thrombin has been added;
   a step 4 of forming a fibrin sheet containing the at least one selected from the group consisting of cells and drugs in a fibrin gel between the substrate and the support film by a reaction between the fibrinogen and the thrombin; and
   a step 5 of melting the substrate at a temperature not lower than a melting temperature of the gelatin hydrogel to separate, from the substrate, the fibrin sheet supported by the support film.

2. The method for producing a fibrin sheet according to claim 1, wherein
   the fibrin sheet is a cell sheet containing at least a cell in the fibrin gel, and
   the substrate is a cell culture substrate.

3. The method for producing a fibrin sheet according to claim 1, further comprising, prior to the step 1, a step of heating an aqueous gelatin solution containing gelatin and water and then cooling the aqueous gelatin solution to obtain the gelatin hydrogel.

4. The method for producing a fibrin sheet according to claim 1, wherein
   the support film is a polypropylene sheet.

5. The method for producing a fibrin sheet according to claim 1, wherein
   the substrate is melted at 30 to 40° C. in the step 5.

* * * * *